United States Patent [19]

Ison

[11] Patent Number: Plant 7,314

[45] Date of Patent: Sep. 4, 1990

[54] DARLENE

[76] Inventor: William G. Ison, Rte. 1, Box 19, Hwy. 19, Brooks, Ga. 30205

[21] Appl. No.: 166,252

[22] Filed: Mar. 10, 1988

[51] Int. Cl.[5] ..... A01H 5/00

[52] U.S. Cl. ..... Plt./47

[58] Field of Search ..... Plt./47

*Primary Examiner*—Robert E. Bagwill

*Attorney, Agent, or Firm*—Eugene T. Holmes

[57] ABSTRACT

A cross between the female variety 5-11-3 and the pollen parent variety Carlos to produce an improved variety of muscadine grape.

1 Drawing Sheet

DESCRIPTION OF THE VARIETY

A Cross between the female seed parent 5/11/3 and the pollen parent variety Carlos.

The primary objective of the breeding was to produce an improved variety of muscadine grape; the fruit of which was to have superior characteristics. These characteristics include large size, high quality, dry scar for longer shelf life, flavor, high sugar content; and the plant to be vigorous and productive.

In comparison to the seed parent 5/11/3, the new variety is sweeter, and larger; but resembles in color and vigor the pollen parent Carlos. The fruit of the new variety contains on the average of from 23.50 to 24.50 percent soluble solids, which sugar content is higher than the sugar content of the fruit of the pollen parent. The present variety yields on the average of 5 to 8 tons per acre in tests conducted at Ison's Nursery & Vineyards, Brooks, Ga.

Asexual reproduction of the new variety either by soft wood cuttings or by layering as performed at Brooks, Ga. shows that the foregoing characteristics and distinctions come true to form and are established and transmitted through succeeding propagations.

The accompanying photograph shows a typical specimen of the vegetative growth and fruit of the new variety when the fruit is ripe and ready for picking and as depicted in color as nearly true as it is reasonably possible to make the same in color illustration of the characters.

The following is a detailed description of the new variety:

Species: *Vitis rotundifolia.*
Type: Vine.
Seed parent: Variety 5/11/3.
Pollen parent: Variety Carlos.

Propagation: Holds its characteristics through succeeding propagation by either layering or by softwood wood cuttings.
Ripening: Early to mid season.
Locality where grown: Brooks, Ga.
Fruit borne: In clusters of approximately 5 to 15 berries per cluster.
Fruit size: Extra large 1¼" in diameter, larger than either seed or pollen parent.
Fruit color: Greyed Orange Group, 165C Fan 4, The Royal Horticultural Society, London, England.
Sugar content: 23.50 to 24.50 percent soluble solids.
Shape: Round.
Seed: Average diameter ⅛ inch, average seed per berry 2.65.
Pulp: A. Color group Greyed Green 196C Fan 4 of The Royal Horticultural Society, London, England. B. Consistency, very soft, melting, juicy as compared to most muscadines.
Skin: Medium.
Foliage: Leaf color, Green Group, 138C Fan 3; The Royal Horticultural Society London, England. Leaf size and shape similar to most muscadine vines.
Reproductive organs:
*Pistillate.*—not self-pollinating.
Growth habits: Vine requires support, vine vigorous and productive.
*Canes.*—Medium to large calipers.
Maturity date: Usually ripens about September 15 at Brooks, Ga.
Diseases: Tolerant to Ripe Rot, Black Rot and other muscadine diseases.

This description was made from a muscadine vine grown at Ison's Nursery and Vineyards, Brooks, Ga.

I claim:

1. The new and distinct variety of grape plant, as described and illustrated.

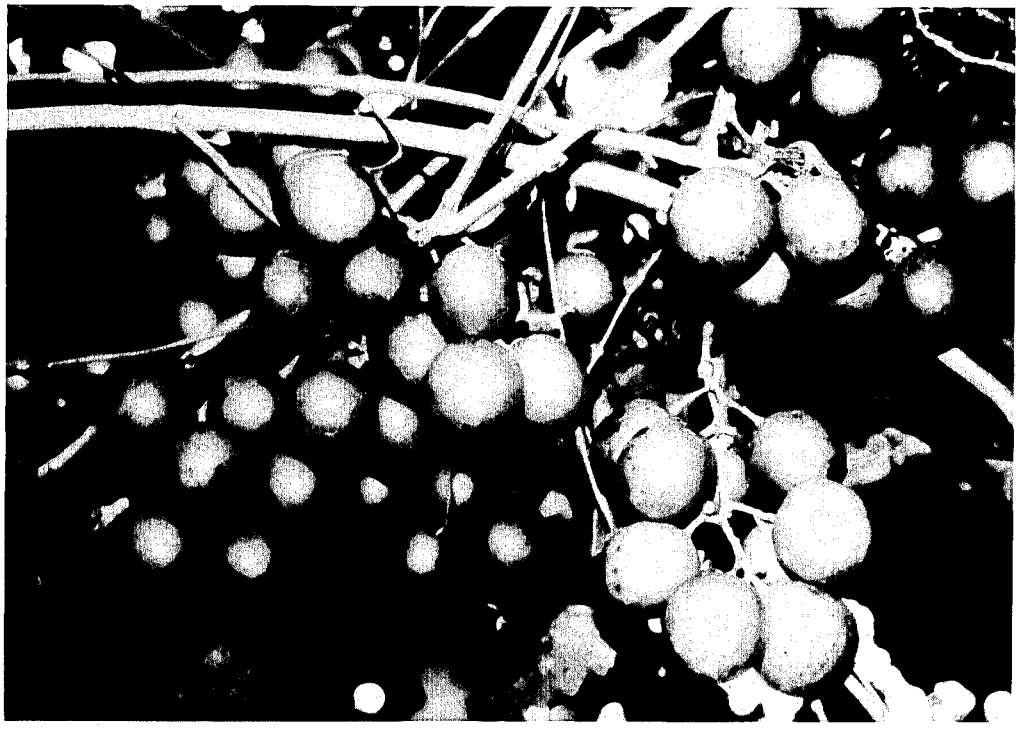

* * * * *